United States Patent
Goroshevskiy et al.

(10) Patent No.: US 8,542,127 B1
(45) Date of Patent: Sep. 24, 2013

(54) APPARATUS FOR THE NON-CONTACT METALLIC CONSTRUCTIONS ASSESSMENT

(71) Applicants: Valerian Goroshevskiy, Moscow (RU); Svetlana Kamaeva, Moscow (RU); Igor Kolesnikov, Moscow (RU); Leonid Ivlev, Moscow (RU)

(72) Inventors: Valerian Goroshevskiy, Moscow (RU); Svetlana Kamaeva, Moscow (RU); Igor Kolesnikov, Moscow (RU); Leonid Ivlev, Moscow (RU)

(73) Assignees: Valerian Goroshevskiy, Moscow (RU); Svetlana Kamaeva, Moscow (RU); Igor Kolesnikov, Moscow (RU)

( * ) Notice: Subject to any disclaimer, the term of this patent is extended or adjusted under 35 U.S.C. 154(b) by 0 days.

(21) Appl. No.: 13/674,118

(22) Filed: Nov. 12, 2012

(51) Int. Cl.
*G01V 3/00* (2006.01)
*G01R 35/00* (2006.01)

(52) U.S. Cl.
USPC .............. 340/657; 73/643; 324/309; 702/106

(58) Field of Classification Search
None
See application file for complete search history.

(56) References Cited

U.S. PATENT DOCUMENTS

| | | | |
|---|---|---|---|
| 6,243,657 B1 * | 6/2001 | Tuck et al. | 702/150 |
| 8,035,372 B2 * | 10/2011 | Garneyer et al. | 324/207.24 |
| 2007/0108973 A1 * | 5/2007 | Lanning et al. | 324/240 |
| 2010/0030491 A1 * | 2/2010 | Ziegel et al. | 702/34 |
| 2010/0321009 A1 * | 12/2010 | Lee et al. | 324/209 |
| 2012/0253696 A1 * | 10/2012 | Pearson et al. | 702/38 |

* cited by examiner

*Primary Examiner* — George Bugg
*Assistant Examiner* — Munear Akki
(74) *Attorney, Agent, or Firm* — Nadya Reingand (57) ABSTRACT

A device and method for discovering, identification and monitoring of mechanical flaws in metallic structures is disclosed, based on magneto-graphic/magnetic tomography technique to identify stress-related defects. The technique is specifically optimized for extended, not-accessible underground and underwater metallic structures quality control, emergency alarms as well as timeline planning for structural repairs and maintenance work. Examples of the technique implementation include pipes for oil and gas industry, detection of flaws in rolled products in metallurgical industry, welding quality of heavy duty equipment such as ships, reservoirs, etc. It is especially important for loaded constructions, such as pressured pipes, infrastructure maintenance, nuclear power plant monitoring, bridges, corrosion prevention and environment protection.

17 Claims, 4 Drawing Sheets

APPARATUS FOR THE NON-CONTACT METALLIC CONSTRUCTIONS ASSESSMENT

CROSS-REFERENCE TO RELATED APPLICATION

This application is a continuation-in-part of the U.S. patent application Ser. No. 13/662,427 filed on Oct. 27, 2012.

FIELD OF INVENTION

The present invention relates broadly to a device and method for continuous (extended) metallic structures inspection and monitoring for possible mechanical defects; in particular, to magneto-graphic quality control devices and methods, such as magnetic tomography, providing a real-time structural status as well as a priority order for immediate and long-term repairs and maintenance work required.

BACKGROUND OF THE INVENTION

This invention can be used in various fields where constructions are tested for continuity defects in not-so-easily accessible areas. Examples of device and method implementation may include pipes for oil and gas industry, detection of flaws in rolled products in metallurgical industry, welding quality of heavy duty equipment such as ships and reservoirs, etc. It is especially important for inspection of loaded constructions, such as pressured pipes, infrastructure maintenance, nuclear power plant monitoring, bridges, corrosion prevention and environment protection.

Similar to the modes of transportation like roads, railroads, and electric transmission lines, the pipelines have an important role in the nation's economy, belonging to the long linear assets. They typically cross large distances from the points of production and import facilities to the points of consumption. Like the other modes of transportation, pipelines require very large initial investment to be built, having long exploitation periods when properly maintained. Like any engineering structure, pipelines do occasionally fail. While pipeline rates have little impact on the price of a fuel, its disruptions or lack of capacity can constrain supply, potentially causing very large price spikes. That's why pipelines, such as ones used in the oil and gas industry, require regular inspection and maintenance before potentially costly failures occur.

The major causes of pipeline failures around the world are external interference and corrosion; therefore, assessment methods are needed to determine the severity of such defects when they are detected in pipelines. Pipeline integrity management is the general term given to all efforts (design, construction, operation, maintenance, etc.) directed towards ensuring continuing pipeline integrity.

Traditional method of assessing the structural integrity typically complemented by flaw detection using in-line inspection (ILI), detecting and evaluating various metal defects organized by area (clusters), assessing their danger by calculating a level of stress-deformed state (SDS), and deciding on a permissible operating pressure with evaluated factor of repair (EFR), based on residual pipe wall thickness (for defects of "metal loss"—corrosion type).

As a contact technique, pigging devices has been used for many years to maintain larger diameter pipelines in the oil industry. Today, however, the use of smaller diameter pigging devices is increasing in many plants as plant operators search for increased efficiencies and reduced costs. Unfortunately, the ILI using intelligent pigging is unavailable for a wide range objects that require full disruptive inspection and significant spending on repair preparation. While the ILI method is suitable for the initial flaw detection, it is less efficient for the relative degree (ranking) of the risk-factor evaluation, as well as for defective pipeline serviceability calculation.

Pipe-line pigging device can detect the following types of defects: i) changing in geometry: dents, wavy surface, deformed shape of cross-section; ii) metal loss, having mechanical, technological or corrosion nature; material discontinuity: layering and inclusions; iii) cracks; iv) all types of welding defects.

Pipe-line pigging is a very expensive and labor-consuming method. The major limitation of this method is the fact that a large part of pipe-lines are not prepared for the pigging device operation, e.g. due to lack of input/output chambers for pig-flow device launching and pipe-line cleaning access, partially blocked pipe cross-section due to the welding artifacts, geometrical abnormalities and large slopes (small radius turns) of the pipe-line layout. In order to make the pipe-line pigging method possible, a significant preparation has to be done in advance, in particular, the high residual level magnetization (saturated magnetic fields) of the pipe-line has to be performed before using the pig-flow device. This causes future technical problems of the pipeline demagnetization that required for actual pipe repair after the pigging.

Moreover, the evaluation of the absolute values of mechanical flaws by pigging device is particular difficult due to the multiple additional factors that have to be taken into account, e.g. bearing capacity of the soil, local cyclical loads (temperature, etc.).

Typically, a pipeline company will have a thorough pipeline safety program that will include a routine for the identification of pipeline defects and review of pipeline integrity. Such a plan should include, but not be limited to: i) a review of previous inspection reports by a third party expert; ii) excavation of sites identified by this review for visual examination of anomalies; iii) repairs as necessary; and iv) addressing factors in the failure and verify the integrity of the pipeline.

It is important to mention that the pipeline safety program can be only as effective as the interpretation of internal inspection reports.

There are several magnetographic devices that have been disclosed for non-destructive inspection of ferrous materials. In magneto-graphic inspection and defectoscopy the tested area of the material is placed in proximity to the magnetic medium. The changes of the surface-penetrating magnetic flux due to the material flows or deviations can be recorded. The resulting "magnetogram" of the material can provide the information about the location, size, and type of the defect or abnormality. In general, this information can be converted into the report about the quality of the material. Obtaining the magnetogram (magnetic picture) of the material in the course of the non-destructive inspection process is very challenging and typically requires additional forms of inspection, such as roentgenogram or an X-ray image.

For example, U.S. Pat. No. 4,806,862 (Kozlov) offers a contact method of magnetographic inspection of quality of materials, where a magnetic substance (such as liquid) is applied to be magnetized together with the tested material. According to the invention, the intensity of the magnetizing field is established by the maximum curvature of the surface of a drop of a magnetic fluid applied onto the surface of the material to be inspected, so that the resulting magnetogram can be used to assess the quality of the material.

In another magnetographic U.S. Pat. No. 4,930,026 (Kljuev), (also cf., USSR Inventor's Certificate No. 482,669, Cl. GOIN 27/89, published in "Biulleten Izobretny" No. 32, 1975), the flaw sensor for magnetographic quality inspection is disclosed, which includes a flaw detector and a mechanism for driving the magneto-sensitive transducer. During the scanning procedure, the magnetic leakage fluxes penetrate through the surface of the material in places where flaws occur, resulting in a magnetogram of the tested material.

There is another magnetic technique has been proposed by U.S. Pat. No. 6,205,859 (Kwun) to improve the defect detection with magnetostrictive sensors for piping inspection. The method involves exciting the magnetostrictive sensor transmitter by using a relatively broadband signal instead of a narrow band signal typically used in order to avoid signal dispersion effects. The amplified detected signal is transformed by a short-time Fourier transform providing the identifiable signal patterns from either defects or known geometric features in the pipe such as welds or junctions. Underwater pipelines inspection by magnetosptictive sensors in described in U.S. patent application Ser. No. 13/336,302 by the authors of the present invention.

There is also a Russian technical standard (GOST), [РД 102-008-2002], certifying the technical condition of the pipe-line based on the results of the remote magneto-metric measurements. The defect areas risk-factor criteria and ranking (such as material stress: F-value) is used for planning a required sequence of repair and maintenance steps. Such criteria were developed by comparison of a risk-factor calculated using the defect geometry in calibration bore pits with a predicted risk-factor obtained by the remote magneto-metric data (i.e. comprehensive F-value of particular magnetic anomaly).

The deviations of F-value can be classified as follows: X1—for negligible defects (good technical condition of the metal); X2—for defects that require a planned repairs (acceptable technical condition); X3—for defects that require immediate repairs (unacceptable, pre-alarm technical condition, alarm).

The absolute values X1-X3 of the F-value (comprehensive value of magnetic field anomaly) should be defined for each particular case, depending upon the following factors: i) Material (e.g. steel) type; ii) Topological location with the local background magnetic fields variation range, iii) Distance to the object (e.g. pipe-line installation depth), iv) General condition of the deformation-related tension within construction under testing, v) etc.

As a result, the only relative changes (variations) of the magnetic field can be evaluated for the given defective segment (relatively to the flawless segment), by comparison its relative F-values. Thus, the very moment of the ultimate stress-limit crossing can be identified for each defective segment during the real operation (i.e. under pressure/loaded) condition. It can be done by monitoring the development of the defects within its F-value interval, namely, starting from the good technical condition X1 up until the yield-strength-limit approaching and material breakdown. It provides a real possibility to predict the defect's speed development, resulting in increased accuracy in priority order definition for upcoming maintenance steps.

The aforementioned techniques are not satisfactory to be used for efficient prediction in defects development timeline and not capable of providing a real-time alert about the strength-limits approaching, i.e. when probable construction failure is about to occur.

The closest technology to the disclosed invention is shown in RU 2264617, describing the Magnetic Tomography (MT) technique of 'Contactless Pipe-line Defect Discovering, Localization and Device Doing the Same'. This technique includes a remote magnetic field vectors measurement in Cartesian coordinates with the movement of measuring device (magnetometer) along the pipe-line, the recording of the anomalies of magnetic field (on top of background magnetic field), processing of the data and report on found pipe-line defects with their localization shown in resulting magnetogram. The technique provides a good sensitivity, also capable of discovering the following types of defects: i) Changing in geometry: dents, wavy surface, deformed shape of cross-section; ii) Metal loss, having mechanical, technological or corrosion nature; material discontinuity: layering and inclusions; iii) Cracks; iv) Welding flaws including girth weld defects. Moreover, such method provides a risk-factor (standard РД 102-008-2002) ranking of the discovered pipe-line defects accordingly to material tension concentration (factor F). Accordingly this technique was taken as initial prototype for the disclosed technology.

MT determines the comparative degree of danger of defects by a direct quantitative assessment of the stress-deformed condition of the metal. Conventional surveys only measure the geometrical parameters of a defect. Their subsequent calculations to assess the impact of the defect on the safe operation of the pipe do not take into consideration the stress caused by the defect. Therefore conventional surveys may fail to detect dangerously stressed areas of the pipe or, conversely, classify a defect as one which requires urgent attention when, in reality, the stress level may be low and the defect presents no immediate threat to the operation of the pipe. Since MT directly measures the stress caused by defects it is an inherently more accurate guide to the safe operation of the pipeline than conventional survey methods.

There are several methods for integrity assessment of extended structures (e.g. metallic pipes) that have been proposed in literature. Thus, U.S. Pat. No. 4,998,208 (Buhrow, et al) discloses the piping corrosion monitoring system calculates the risk-level safety factor producing an inspection schedule. The proposed system runs on a personal computer and generates inspection dates for individual piping elements. Corrosion data for individual inspection points within each circuit is used to estimate likely corrosion rates for other elements of the particular circuit. It translates into risk factors such as the toxicity, the proximity to the valuable property, etc. The system evaluates a large number of possible corrosion mechanisms for each inspection point providing a very conservative inspection date schedule.

There is another method disclosed in U.S. Pat. No. 6,813,949 (Masaniello, et al.), which addresses a pipeline inspection system having a serviceability acceptance criteria for pipeline anomalies, specifically wrinkles, with an improved method of correlating ultrasonic test data to actual anomaly characteristics.

There is a also known procedure of planning a sequence of repair and renovation steps to be applied to the defective segments of heating infrastructures and buildings (RU 2110011 C1 (21) 95112182 (22) 13 Jul. 1995 published 27 Apr. 1998). This method offers Infra-red imaging of the constructions under testing, defining the defective areas, digitizing their images and evaluating the excessive heat produced by defective areas. The resulting data leads to the planning of a sequence of steps required for repairs.

The disadvantage of this method is a limited area of application where the heat-transferring objects, such as heating infrastructure, are present. Moreover, this method is effective only at the stage when the fracture and leakage have already been developed, causing the excessive heat radiation around the defective areas.

There are several methods for non-destructive testing of pipes have been known. Thus, US20060283251 (Hunaidi)

suggests non-destructive condition assessment of a pipe carrying a fluid by evaluating the propagation velocity of an acoustic disturbance between two remote points on the pipe. A corresponding predicted value for the propagation velocity is computed as a function of the wall thickness.

Another non-destructive method U.S. Pat. No. 4,641,529 (Lorenzi, et al) discloses pipeline ultrasonic transducers in combination with photographic device for corrosion detection. Such ultrasonic transducer(s) produce a parallel beam for direction toward the pipe wall from inside a pipe, with a sufficiently large beam width to permit comparison of time displayed signal components in defect depth determination, with the signal propagating through a gaseous medium.

There is another method for estimating worst case corrosion in a pipeline is disclosed in U.S. Pat. No. 7,941,282 (Ziegel, et al), in which non-destructive pipeline wall thickness measurements are performed by sampled (at locations) ultrasonic and/or radiography (UT/RT) measurements. A distributed ILI data library for test pipelines is calibrated to correspond to UT/RT measurements for inspection. After sampling, the candidate statistical distributions are evaluated to determine which of the candidate most accurately estimates the worst case corrosion measured by ILI.

There is a known method for repair sequence planning based on possible (metal pipe) defects location and cause discovering by detecting anomalies in the magnetic field of pre-magnetized pipeline with special devices, such as pig-flow defectosopes, (RU No 2102652, 6F 17D5/00, published 1998).

Such method include a pipe-line setup with defectosope input-output chambers and a pig-flow device itself, as well as internal pipe-line surface cleaning means to provide the open cross-section needed to launch the pig-flow device. The method also requires a simultaneous magnetization of the pipe-wall along the pig-flow device movement and registration of anomalies based on scattering and saturation of the magnetic field, recording and processing of the information to conclude about defects location and nature.

As an example, another method can also be considered: RU2139515 filed Dec. 23, 1997). This method of evaluation of the material vulnerability and residual operation resource relies on the measured dependence between the mechanical (structural) defects (related to steel resistance) and steel parameters measured by non-destructive means, such as value of magnetic permeability measurement.

The, the technological outcome of present invention would include:

1) Expanding the implementation area, including not only the heating infrastructure and buildings but also various types of extended structures of metallic materials, including not-through defects in stage of development.

2) Increasing the reliability and accuracy of information about repair procedures suggested schedule. It can be done using the risk-factor ranking tables based on the absolute values of stress, compared against the values from regulatory documentation (for particular object).

3) Increasing the efficiency of the method by applying a visualization-assisted maintenance and repair schedule (with the real values of mechanical stress) to the actual structural layout, such as a pipe-line integrated into the existing topology, for example.

Such technological outcome can be achieved, mainly, due to the following innovative means: i) Remote (from the ground surface, non-destructive) identification of the defects and their respective risk-factors, by using improved measurements of the local mechanical stresses; ii) Remote identification of operational parameters for the defective segments of the structure, by using the absolute local stress values, compared against the values from regulatory documentation (for particular object). iii) Graphical visualization of the obtained information using the actual topological layout of the area and the structure in absolute geographical coordinates.

SUMMARY OF THE INVENTION

A device for discovering, identification and monitoring of mechanical defects in metallic structures is disclosed. The device includes a sensor array registering a signal, a signal representing a density of magnetic field strength distribution along the metallic structure and an analogue-to-digital converter digitizing the signal. The device also includes a calculation unit that receives and analyzes the signal in order to provide an identification of signal anomalies. This identification is based on a magnetic tomography method that employs a known inverse magnetostrictive Villary effect of changing the magnetic susceptibility under applied mechanical stress resulting in distribution of magnetic field gradient along the structure surface. The distribution of magnetic field, in turn, provides information about the presence and the value of the magnetic field anomaly at the given location of the structure.

The sensor within the device can be built as a 3-dimensional array, providing a 3-dimensional distribution of the signal anomaly within a measurement area. After the sensor, the signal is first recorded by a memory unit and later processed by the calculation unit for more accurate and reliable results.

The calculation unit is capable of communicating with the sensor array remotely and is connected to light- and/or sound-means in order to alarm an operator about the signal anomaly value in a real-time situation, if needed.

To further support the identification, the obtained signal can be compared with pre-determined technological information, such as look-up tables, standards, thresholds, or calibrated using an alternative method, such as a contact bore pit measurement.

The device is also includes the information visualization unit for representing the signal anomalies along with the topology of the metallic structure under testing. A Global Positioning Sensor unit can be used for simultaneous recording of anomalies coordinates. Moreover, a Gyroscope and/or accelerometer unit can also be used for the sensor angle position measurement.

The device can be used in various situations and for various extended metallic objects, such as a (unpiggable) pipeline, a cable, a rail, a rolled metal product, a reservoir, a bridge or a vessel. Generally, such objects can be located underwater or underground and the identification can be performed through a ground or water layers, without interruption of the object regular operation.

The device can also be powered by the battery for field measurements, with the battery-charge monitoring incorporated into the device.

DETAILED DESCRIPTION OF THE PREFERRED EMBODIMENT

The present invention describes the magnetic tomography (MT) device for magnetographic identification and analysis of mechanical flaws/defects, optimized for extended metallic constructions inspection. The block-diagram of the method is given in FIG. 1.

The magnetic tomography device is based on using of the inverse magnetostrictive (Villary) effect—i.e. the changing of the material magnetic susceptibility under applied mechanical stress. Generally, such technique uses "natural" magnetization of the ferrous pipes by magnetic field of the Earth.

The use of MT device has following advantages: 1) Applicable for the unpiggable pipelines or other objects where in-line inspection method is inapplicable; 2) the objects to be inspected include but not limited to: compressor stations pipelines, pipeline inclusions, water-supply pipelines in cities; 3) the use of MT device doesn't require any preparation of the pipeline for testing such as cleaning, opening the pipe, or stopping pipeline operation; 4) the use of MT device doesn't require magnetizing of the object's pipes; 5) MT device capable of detecting flaws of various types including long crack-like pipe-line defects and welding defects; 6) the use of MT device doesn't have limitation on the structure diameter, configuration and protective coatings, for example, change of pipe diameter/wall-thickness, turns and their directions, transported product (e.g. gas, oil, or water), inside pressure, pipeline protection (e.g. cathodic protection, etc).

The MT device is capable to evaluate the degree of danger of defects by the level of concentration of mechanical tensions rather than defect geometry (e.g. length-width-depth).

The MT device is particularly suitable for running a database on condition certification of objects of any length and any monitoring period.

The MT device implementation guarantees minimal customer resources use for monitoring preparation and repair works such as: i) reduces work volume and total costs of pipe access works; ii) greatly reduces time of full diagnostic-repair evaluation-repair planning-repair cycle; iii) gives pipe corrosion prognosis and estimates levels of tense-deformed state of the pipeline under current operating conditions.

Figure 1:
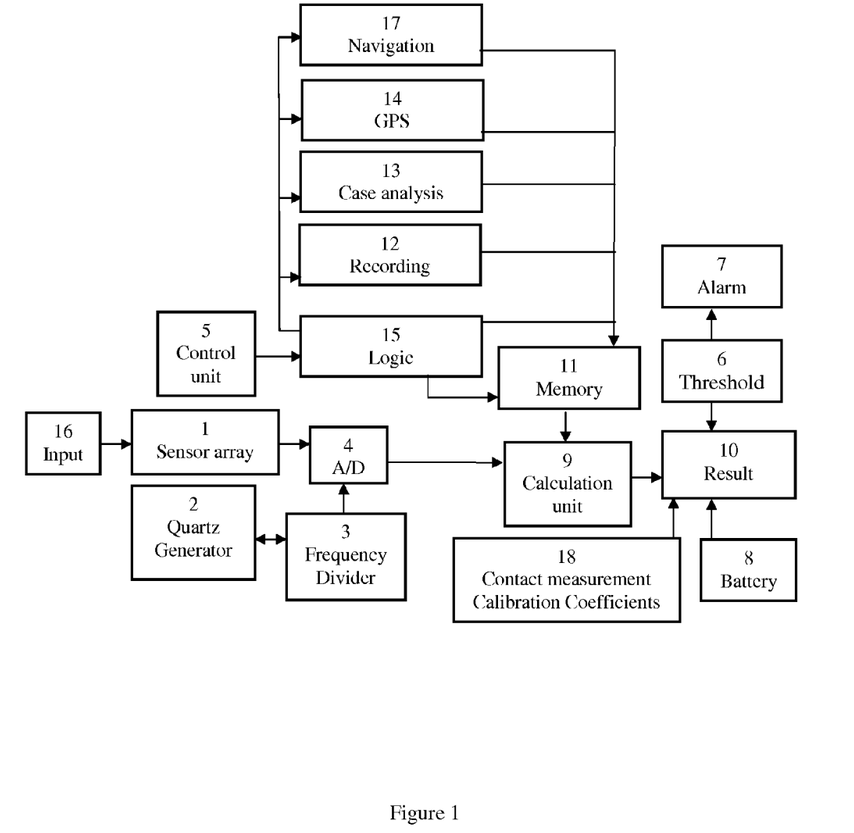
FIG. 1: The block-diagram of the device for non-contact discovering, identification and monitoring of mechanical defects in metallic structures.

The MT device application provides a non-contact metal flaws monitoring, which is particularly suitable for hidden (underground/underwater) ferromagnetic constructions of extended length. The block-diagram of such device is shown in FIG. 1.

The registration of magnetic field anomalies in extended metallic structures (such as a pipe) is performed in predetermined coordinate system relatively to the structure (axis) with a known (fixed) sensor array aperture. The coordinates of each single measurement along the structure can be chosen accordingly to the cross-section size and burial depth of the (underground, underwater) structure. It results in the matrix distribution of magnetic field gradient along the structure surface area under each single measurement. The presence and the value of the magnetic field anomaly at the given location are derived from the comparison of different increments of the Earth's magnetic induction vector modulus.

The MT device comprises of a sensor array (1), a quartz generator (2), a frequency divider (3), analogue-to-digital converter (A/D) (4), a control unit (5), a threshold unit (6), a light- and sound-alarm unit (7), a battery charge indicator (8), a calculation unit (9), a (resulting) information visualization unit (10), a memory unit (11), a recording unit (12), a case-analysis unit (13), a GPS unit (14), navigation unit (gyroscope/accelerometer) (17) and a logic unit (15). The device performs in a following manner:

The sensor array (1) registers induction gradients of the magnetic field (16) within construction under testing.

By using A/D converter (4), a digitized signal is: i) inputted into calculation unit as a preliminary data; ii) recorded by the memory unit (11). The Quartz generator (2) controls the frequency of the A/D converter (4).

The control unit (5) through the logic unit (15) controls the case analysis unit (13) with predetermined database and lookup tables, the recording unit (12), the GPS unit (14), the navigation unit (17) and the memory unit (11). The calculation unit receives the information from units (12), (13), (14), (17) through the memory unit (11), controlled by logic unit (15).

The real-time information from (4) is compared with the information from the threshold unit (6). By these means, the visualization of the real-time data against the threshold values is provided, enabling the alarming (by the unit (7)) an operator about potentially dangerous operational conditions of the structure. The remaining charge of the battery is monitored by (8). The calculation unit (9) is responsible for the information processing, providing the information to the resulting and visualization init (10). the resulting and visualization init (10) also accommodates inputs from the threshold unit (6) and the light-/sound-alarm unit (7) which enables identification of the parameters' deviation from the background level, as well as (e.g. wirelessly) informing an operator about the deviation value in real-time, respectively.

Moreover, the resulting and visualization init (10) is capable of receiving the results of the predetermined in-contact measurement (e.g. extracted from the local bore pit at the underground pipe) in a form of calibration coefficients in order to calibrate the calculated data of found magnetic anomalies.

The situational case-analysis unit (13) enables the analysis of the information in the context of pre-determined technological information and schemes, which, in combination with the GPS unit (14), provides more accurate topological mapping.

In the preferable configuration of the device, a GPS sensor (14) is complemented by a navigation unit that includes gyroscope(s) and/or set of accelerometer(s) (17), enabling the recording of the device's angle-positioning relatively to the extended metallic structure cross-section at each moment of the magneto-graphical measurements. The recorded angle-positioning data (including positioning relatively to horizon) is used further to correct the magneto-graphical measurements due to structural bending/turning-related deviations.

Accordingly, the absolute coordinates of discovered defects relatively to the (visible) reference objects can be obtained with the following registration in the database during the equipment assessment report.

In the preferable configuration of the mentioned device, each sensor array (1) consists of a few 3-component arrays, positioned along the 3 orthogonal dimensions. Alternatively, each array includes a few single-component sensors, such as optically pumped quantum analyzers. Using the optically pumped quantum analyzers in the sensor array (1) allows higher flaw-detection accuracy in underground constructions, well-suited for detecting relatively small values of mechanical stress, and/or deeper underground installation.

Since the sensor array (1) can be rotated above the surface of the structure during the scanning procedure, it is possible to implement a polar coordinate system for defects detection, in combination with the data from the gyroscope/accelerometer unit (17).

The recording process is arranged in a discrete manner, enabling an independent storage and access for different recorded portions (memory segments) of the scanning.

In the preferable configuration of the mentioned device, the unit (9) calculates: i) magnetic field gradients distributed along the square area within the defined segment of the structure, ii) the values of the local mechanical stress within the defined segment of the structure.

In the preferable configuration, the disclosed device shown in FIG. 1 is realized similarly to the device disclosed in RU2264617.

In the alternative configuration of the disclosure, the calculation unit (9) can be realized similarly to the U.S. Pat. No. 4,309,659.

Moreover, in the alternative configuration of the disclosure, the recording unit (12) can be realized similarly to the RU2037888 patent.

Figure 2:
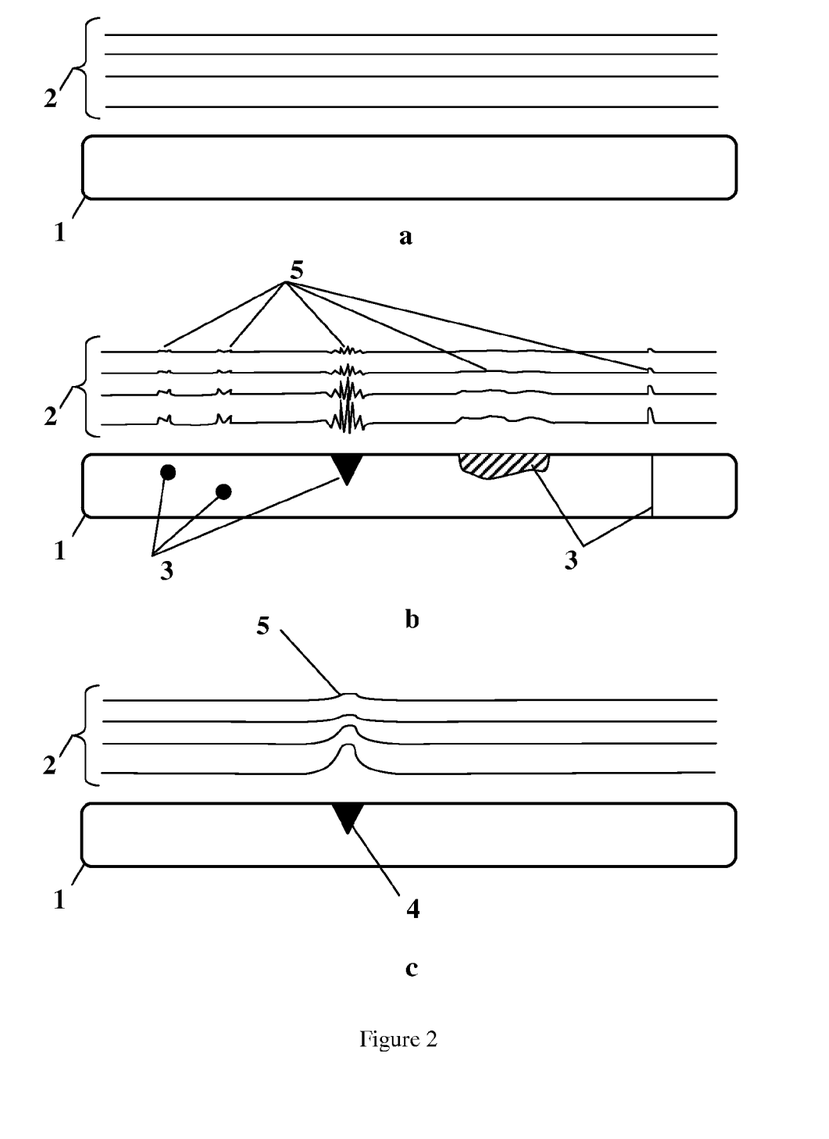
FIG. 2: A principle of operation of the magneto-graphic technique used in metallic structure defects monitoring and integrity assessment.

The principle of operation of the device shown in FIG. 1 is explained further in FIG. 2. The FIG. 2a shows the structure (1) without defects, with the preliminary magnetic tomography charts (magnetogram) (2) showing the measured background (calibrated to zero) level of magnetization. The FIG. 2b show the same structure (1) with the potential defects (3), (4) corresponded to the deviations of the tomography charts (5). The FIG. 2c show the same structure (1) with the processed tomography charts (5), showing the location of the defect (4) that require an immediate attention (unacceptable, pre-alarm technical condition, alarm), based on the local mechanical stress value estimate.

As mentioned before, the magnetogram (2) attributes and characterizes the section of the structure by registering and analyzing changes in the magnetic field of the structure such as pipeline. These changes are related to stress, which, in turn, is related to defects in the metal and insulation. Magnetic measurements data is collected from the surface and includes the detected anomalies. Such detected anomalies are function of a local stress and/or local mechanical tension and structural changes in the metal. Moreover, a post-processing of this experimental data enables the visualization of the flaws in the structure.

The described MT device does not measure the dimensions of geometric defects alone, but, instead, provides a stress measurement caused by these defects and identifies their character, location and orientation in accordance with the location and orientation of the area of stress. Linear and angular coordinates of flaws in the metal and coating are have been experimentally defined within a tolerance of +/−0.25 m.

The device explained by FIG. 1 and FIG. 2 can effectively identify and analyze the magnetic field anomalies in areas with stress concentrators caused by: i) defects or changes in structural conditions (such as metal loss, cracks, dents, lamination and inclusions); ii) erosion, seismic activity, or third-party damage.

The functionality of the device in FIG. 1 and FIG. 2, can further being explained by the following example. The particular MT measurement point was located at 1150 feet away from the scanning starting point. The signal value from the local anomaly was appeared to be 3.5-times larger than the local background value for seven consequent measurements. Two flaws, both caused by a metal deformation, had been determined by processing the signal profile.

Figure 3:
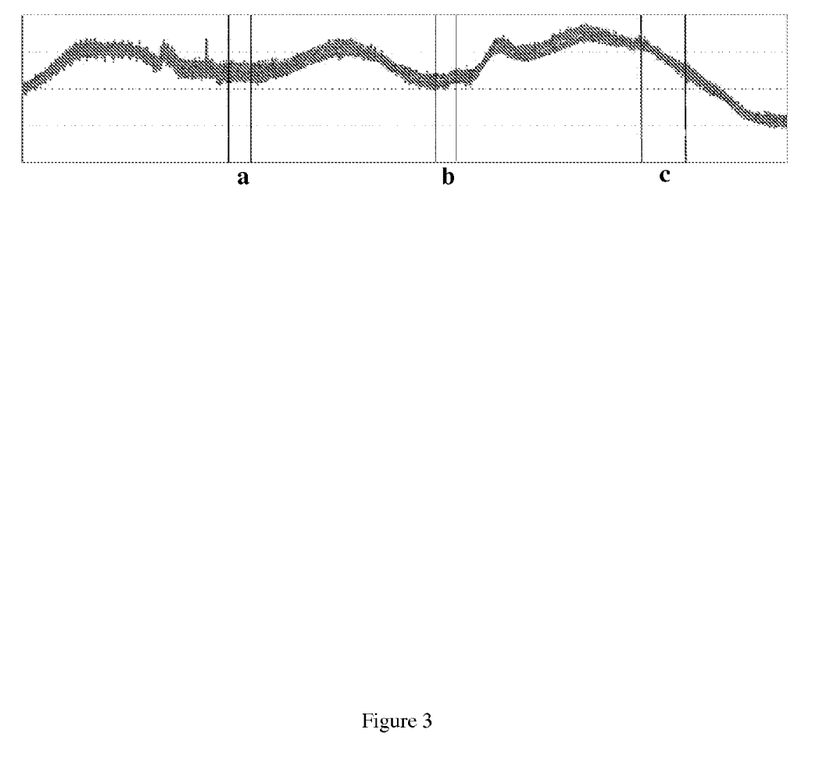
FIG. 3: An example of a single magneto-graphic measurement. The diagram represents the three areas of a magnetic field anomalies (a), (b) and (c) corresponding to the respective local mechanical stresses. The area (c) shows the evidence of the metal stress yielding-limit crossing.

FIG. 3 shows the example of a single magneto-graphic measurement. The diagram represents the three areas of a magnetic field anomalies (a), (b) and (c) corresponding to the respective local mechanical stresses. The area (c) shows the evidence of the metal stress yielding-limit crossing.

Based on this analysis, the construction opening (a local bore pit for underground pipe) had been performed for visual (and contact) defectoscopy at the location (c). The actual dimensions of defects (cracks and corrosion) have been evaluated. The magnetographic device calibration has been done based on a difference between the measured signal (versus background) and the actual parameters of the defect (s) found. Then, the calibrated values of the anomalies have been used as a criterion. For this particular case, the calibrated values appeared to be 3-10 times higher comparing to the background signal value. The follow-up magnetographic measurements have been performed in a real-time.

The presented MT device helps to plan necessary structural maintenance procedures and define their priorities. The device is particularly efficient when the magneto-graphic material (Magnetic Tomography) inspection is applied to extended metallic constructions, revealing its flaws against the topological map of the structure.

Moreover, the device enables direct monitoring of the defective construction segments with still acceptable technical conditions. It allows a long-term database support for the follow up monitoring, certification, prognosis and operational timeline for the structure.

Figure 4:
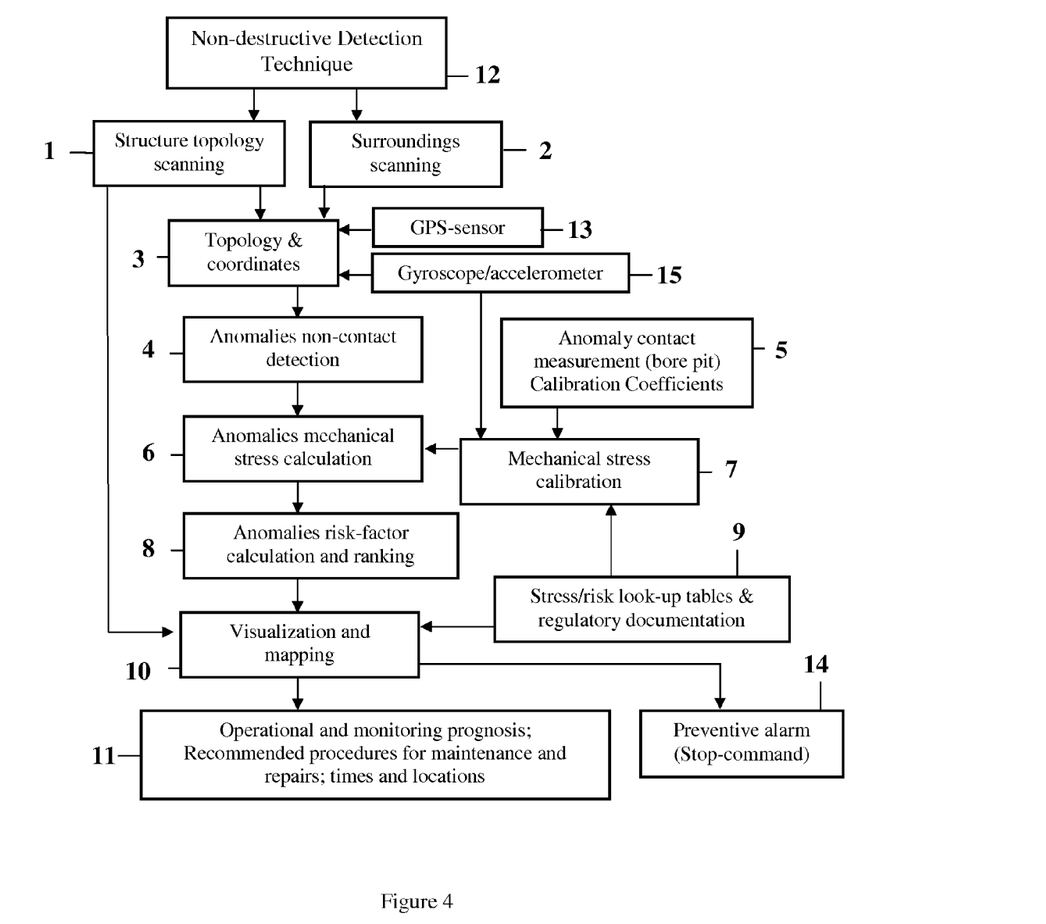
FIG. 4: Block-diagram for metallic structure integrity assessment and maintenance planning method.

The present invention also describes the magnetographic method maintenance timeline planning method (priority steps), optimized for extended metallic constructions. The block-diagram of the method is given in FIG. 4.

The method includes (with reference to FIG. 4): Precise scanning (1) using the non-destructive magneto-graphic (such as MT) anomalies detection technique (12) for (axial) localization of the extended metallic structure (e.g. subterranean or submarine pipeline), as well as surrounding scanning (2) for identification of other possible objects in the vicinity of the structure, including hidden objects (pipes, cables) detection (4) and identification of the defective segments or areas of the said structure, in general, by using thermo-visual imaging, magneto-graphic methods or by other remote (non-contact, non-destructive) methods; accurate location of different types of anomalies by using thermal and magnetic non-contact scanning sensors moving in Cartesian coordinates. Registering and processing of the obtained data and assessing resulting anomalies in accordance with their risk-factor and structural topology (mapping) (3). Identification of the absolute geographical coordinated for characteristic elements of the construction under testing (3), preferably by using a GPS sensor(s) (13) and (inertial) navigation system (gyroscope and/or accelerometers) 15. Non-contact detection (4) of the construction defects and flawless segments. In-contact measurement of at least one found defect (5) (e.g. visual, spectral, magneto-graphic). Calculation of the local metal stress at each found anomaly (6) and calibration (7), using calibrating coefficients obtained by in-contact method (5) and regulatory documentation and stress/risk look-up tables (9). Processing the obtained information about discovered defects and its ranking accordingly to the risk factor (value of mechanical stress) (8). Graphical visualization of the results in the form of the topological map of the construction using absolute values of geographical coordinates (10). The topological map would reflect the maintenance schedule to be applied to the construction following from the recorded mechanical stress values at the defective segments of the construction (9), (10). The method includes preventive warning means (14) to inform about defects that require immediate attention, e.g. unacceptable operational condition. The aforementioned method provides operational and monitoring prognosis (11) with an optimal priority planning for required maintenance steps for construction under testing.

In the preferred embodiment of the invention the non-destructive detection of anomalies in the structure is performed using magnetographic technique such as Magnetic Tomography.

The purpose of the present invention is to improve the technique RU 2264617, by overcoming: i) The lack of quantitative criteria for risk-factor real-time assessment and ranking required for proper planning of correct sequence of repair and maintenance procedures; ii) Low sensitivity in linear coordinate measurements without explicit geographical location information; ii) The limited visualization and visualization-assisted analysis options within the structural layout.

The main goals of the present invention are: i) to increase the method's applicability area; ii) to increase the accuracy of the priority scheduling for required maintenance and repair procedures; iii) to broad the spectrum of the potentially scheduled repair procedures, based on the additional data.

The preferred realization of the method is given below, as an example.

First Step: Detect the accurate location of the underground metallic pipe-line (its axis), as well as possible presence of other objects and structures (other pipes, cables, etc.) see FIG. 1, (1), (2). Use the global positioning unit (13) as well as an angle navigation unit (15) for accurate topological mapping.

Second step: Performing magneto-graphic technique for non-destructive flaws detection in the structure, for example, by obtaining a magnetogram of the structure (4). In particular, the non-contact technique can be used to image magnetic properties of an object by using the eddy current effect for multi-dimensional scanning the internal layers of the metallic structure. The scanning is typically performed multiple (10-1000000) times, providing a 3-dimensional locations of the anomalies after processing (magnetogram).

Third step: Reaching the structure (i.e. in-contact measurement) at the location of one of the detected defective areas (e.g. calibration bore) (5), identification of the type of the most dangerous defects, evaluation of their parameters (by visual, spectral, magneto-graphic methods, for example) and development speed.

Fourth step: Calibrating (7) of the preliminary prognosis for all detected defects (of all types) and associated risk-factors (MIT results) by using additional (complementary) information obtained from the calibration bore explicitly (5). Namely, calibrating (7) the non-contact measurements (4) using calibration coefficients obtained from the at least one in-contact measurement (5). Comparison the calculated mechanical stress (and risk-factors) for these defects with the values from regulatory documentation and standard look-up tables (9). Typically, regulatory documentation consists of numbers that pre-calculated using the risk-factor evaluation algorithms applied to the known geometrical parameters of the known "calibrated" defects.

Fifth step: Searching for identical or similar (by amplitude, area, pattern, etc.) magnetic anomalies within the defective and not-defective segments of the structure.

Sixth step: Processing the detected magnetic anomalies (8) to define qualitative stress indices (i.e. F-value) that are characteristic risk-factor parameters for each found defect (of each type).

Seventh step: Processing (8), (9), (10) of all resulting parameters, using an appropriate software program; calculating the relative risk-factor distribution within each segment of the tested structure by taking into account all detected types of the defects. Evaluating relative distribution of the mechanical stress in vicinity of the defects by using obtained F-values. Estimating (11) the predicted time-line of the defects development and, as a result, recommending (11) a period of safe operation for the structure.

Eighth step: Visualizing the obtained results using the map with the real topological coordinates, depicting the structure, found defects and their corresponded risk-factor-distributions. Recommend the important locations at the map for optimal sequence of maintenance steps to be performed (10), (11). Providing preventive warning (14) to (e.g. wirelessly) inform an operator about defects that require immediate attention, e.g. unacceptable operational condition of the structure.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A device for discovering, identification and monitoring of mechanical defects in metallic structures, comprising:
   a sensor array, registering a signal, a signal representing a density of magnetic field strength distribution along the metallic structure under testing;
   an analogue-to-digital converter digitizing the signal;
   a calculation unit receiving the digitized signal, the calculation unit analyzing the digitized signal and providing an identification of signal anomalies using a magnetic tomography method that is based on the inverse magnetostrictive Villary effect, the effect of changing of material magnetic susceptibility under applied mechanical stress, the changing of magnetic susceptibility resulting in distribution of magnetic field gradient along the structure surface area under testing, the distribution of magnetic field gradient providing an information about the presence and the value of the magnetic field anomaly at the given location of the structure.

2. The device of the claim 1, wherein the sensor array is 3-dimensional providing a 3-dimensional distribution of the signal anomaly within a measurement area.

3. The device of the claim 1, where the signal is first recorded by a memory unit and later processed by the calculation unit for more accurate and reliable results.

4. The device of the claim 1, wherein the calculation unit is located at a distance from the sensor array, and the digitized signal is transmitted to the calculation unit via internet.

5. The device of the claim 1, wherein the calculation unit is connected to light- and/or sound-alarm means of informing an operator about the signal anomaly value in a real-time situation.

6. The device of the claim 1, wherein providing the identification of signal anomalies is supported by a pre-determined technological information being compared with the signal obtained using the magnetic tomography.

7. The device of claim 6, wherein the pre-determined technological information is look-up tables, standards and thresholds.

8. The device of claim 6, wherein the pre-determined technological information is a calibration by an alternative measurement.

9. The device of claim 8, wherein the alternative measurement is a contact bore pit measurement.

10. The device of the claim 1, further comprising an information visualization unit to represent the signal and the signal anomalies along with the topology of the metallic structure under testing.

11. The device of the claim 10, where the signal anomalies are measured simultaneously with the absolute coordinates of the respective anomalies by using a Global Positioning Sensor unit.

12. The device of the claim 10, wherein the signal anomalies are measured simultaneously with the absolute angle position of the sensor array by using a Gyroscope and/or accelerometer unit.

13. The device of the claim 1, wherein the extended metallic structure, where the said metallic structure is a pipe, a cable, a rail, a rolled metal product, a reservoir, a bridge or a vessel.

14. The device of the claim 13, wherein the structure is located underwater or underground, and the identification is performed via a layer of ground or water.

15. The device of the claim 13, wherein the identification of anomalies is performed without interruption of the structure normal functioning.

16. The device of the claim 15, wherein the device being operated by the battery for performing the anomalies identification in field, and the battery having residual charge indicator to ensure a quality and reliability of the identification.

17. The device of the claim 1, wherein the structure is unpiggable pipeline.

* * * * *

(12) EX PARTE REEXAMINATION CERTIFICATE (10788th)
United States Patent
Goroshevskiy et al.

(10) Number: US 8,542,127 C1
(45) Certificate Issued: Jan. 7, 2016

(54) APPARATUS FOR THE NON-CONTACT METALLIC CONSTRUCTIONS ASSESSMENT

(71) Applicants: Valerian Goroshevskiy, Moscow (RU); Svetlana Kamaeva, Moscow (RU); Igor Kolesnikov, Moscow (RU); Leonid Ivlev, Moscow (RU)

(72) Inventors: Valerian Goroshevskiy, Moscow (RU); Svetlana Kamaeva, Moscow (RU); Igor Kolesnikov, Moscow (RU); Leonid Ivlev, Moscow (RU)

(73) Assignees: Valerian Goroshevskiy, Moscow (RU); Svetlana Kamaeva, Moscow (RU); Igor Kolesnikov, Moscow (RU)

Reexamination Request:
No. 90/013,439, Feb. 4, 2015

Reexamination Certificate for:
Patent No.: 8,542,127
Issued: Sep. 24, 2013
Appl. No.: 13/674,118
Filed: Nov. 12, 2012

(51) Int. Cl.
*G08B 21/00* (2006.01)
*G01V 3/00* (2006.01)
*G06F 19/00* (2011.01)
*G01N 27/82* (2006.01)
*G01N 27/85* (2006.01)

(52) U.S. Cl.
CPC ............ *G01N 27/82* (2013.01); *G01N 27/85* (2013.01)

(58) Field of Classification Search
None
See application file for complete search history.

(56) References Cited

To view the complete listing of prior art documents cited during the proceeding for Reexamination Control Number 90/013,439, please refer to the USPTO's public Patent Application Information Retrieval (PAIR) system under the Display References tab.

*Primary Examiner* — Robert Nasser (57) ABSTRACT

A device and method for discovering, identification and monitoring of mechanical flaws in metallic structures is disclosed, based on magneto-graphic/magnetic tomography technique to identify stress-related defects. The technique is specifically optimized for extended, not-accessible underground and underwater metallic structures quality control, emergency alarms as well as timeline planning for structural repairs and maintenance work. Examples of the technique implementation include pipes for oil and gas industry, detection of flaws in rolled products in metallurgical industry, welding quality of heavy duty equipment such as ships, reservoirs, etc. It is especially important for loaded constructions, such as pressured pipes, infrastructure maintenance, nuclear power plant monitoring, bridges, corrosion prevention and environment protection.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-6 and 10-17 are determined to be patentable as amended.

Claims 7-9, dependent on an amended claim, are determined to be patentable.

New claims 18 and 19 are added and determined to be patentable.

1. A device for discovering, identification and monitoring of mechanical defects in metallic structures, composing:
   a sensor array *positioned in three orthogonal dimensions, said sensor array* registering a signal, a signal representing a density of magnetic field strength distribution along the metallic structure under testing;
   an analogue-to-digital converter digitizing the signal;
   a calculation unit receiving the digitized signal, the calculation unit analyzing the digitized signal and providing an identification of signal anomalies using a magnetic tomography method that is based on the inverse magnetostrictive Villary effect, the effect of changing of material magnetic susceptibility under applied mechanical stress, the changing of magnetic susceptibility resulting in distribution of magnetic field gradient along the structure surface area under testing, the distribution of magnetic field gradient providing an information about the presence and the value of the magnetic field anomaly at the given location of the structure.

2. The device of [the] claim 1, wherein the sensor array is 3-dimensional providing a 3-dimensional distribution of the signal anomaly within a measurement area.

3. The device of [the] claim 1, where the signal is first recorded by a memory unit and later processed by the calculation unit for more accurate and reliable results.

4. The device of [the] claim 1, wherein the calculation unit is located at a distance from the sensor array, and the digitized signal is transmitted to the calculation unit via internet.

5. The device of [the] claim 1, wherein the calculation unit is connected to light- and/or sound-alarm means of informing an operator about the signal anomaly value in a real-time situation.

6. The device of [the] claim 1, wherein providing the identification of signal anomalies is supported by a pre-determined technological information being compared with the signal obtained using the magnetic tomography.

10. The device of [the] claim 1, further comprising an information visualization unit to represent the signal and the signal anomalies along with the topology of the metallic structure under testing.

11. The device of [the] claim 10, where the signal anomalies are measured simultaneously with the absolute coordinates of the respective anomalies by using a Global Positioning Sensor unit.

12. The device of [the] claim 10, wherein the signal anomalies are measured simultaneously with the absolute angle position of the sensor array by using a Gyroscope and/or accelerometer unit.

13. The device of [the] claim 1, wherein the extended metallic structure, where the said metallic structure is a pipe, a cable, a rail, a rolled metal product, a reservoir, a bridge or a vessel.

14. The device of [the] claim 13, wherein the structure is located underwater or underground, and the identification is performed via a layer of ground or water.

15. The device of [the] claim 13, wherein the identification of anomalies is performed without interruption of the structure normal functioning.

16. The device of [the] claim 15, wherein the device being operated by the battery for performing the anomalies identification in field, and the battery having residual charge indicator to ensure a quality and reliability of the identification.

17. The device of [the] claim 1, wherein the structure is an unpiggable pipeline *and wherein the device is configured to analyze the unpiggable pipeline*.

*18. The device of claim 1, wherein the device is a non-contact surveying device.*

*19. The device of claim 1, wherein the device is configured to utilize GPS coordinates.*

\* \* \* \* \*